United States Patent
Pavlin et al.

(10) Patent No.: US 6,864,349 B2
(45) Date of Patent: Mar. 8, 2005

(54) AQUEOUS SUSPENSIONS CONTAINING POLYMERIZED FATTY ACID-BASED POLYAMIDES

(75) Inventors: Mark S. Pavlin, Savannah, GA (US); Richard A. O'Brien, Panama City, FL (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 10/319,412

(22) Filed: Dec. 13, 2002

(65) Prior Publication Data

US 2003/0162938 A1 Aug. 28, 2003

Related U.S. Application Data

(60) Provisional application No. 60/396,892, filed on Jul. 16, 2002, and provisional application No. 60/341,538, filed on Dec. 13, 2001.

(51) Int. Cl.$^7$ .................. C08G 69/08; C08G 69/34; C08K 3/20; C08L 77/00
(52) U.S. Cl. .................. 528/310; 528/322; 528/339; 528/339.3; 524/600; 524/601; 524/602; 524/606; 524/608; 524/800; 524/801
(58) Field of Search ................. 528/310, 322, 528/339, 339.3; 524/600–602, 606, 608, 800, 801

(56) References Cited

U.S. PATENT DOCUMENTS

| | | | |
|---|---|---|---|
| 5,324,812 A | 6/1994 | Speranza et al. | 528/338 |
| 5,466,734 A | 11/1995 | Catena et al. | 524/230 |
| 5,886,135 A | 3/1999 | Fischer et al. | 528/329.1 |
| 5,948,880 A | 9/1999 | Fischer et al. | 528/339.3 |
| 5,962,629 A | 10/1999 | Corley et al. | 528/341 |
| 5,998,508 A | 12/1999 | Corley et al. | 523/414 |
| 6,013,757 A | 1/2000 | Corley et al. | 528/289 |
| 6,077,900 A | 6/2000 | Boudreaux et al. | 524/501 |
| 6,103,809 A | 8/2000 | Ahmed et al. | 524/489 |
| 6,165,971 A | 12/2000 | Oppenländer et al. | 510/502 |
| 6,268,466 B1 * | 7/2001 | MacQueen et al. | 528/335 |
| 6,402,408 B1 * | 6/2002 | Ferrari | 401/64 |
| 6,497,861 B1 * | 12/2002 | Wang et al. | 424/64 |
| 6,503,077 B2 * | 1/2003 | Orth et al. | 431/288 |

FOREIGN PATENT DOCUMENTS

| | | |
|---|---|---|
| DE | 19750246 | 5/1999 |
| EP | 0374332 | 6/1990 |
| EP | 0958811 | 11/1999 |
| EP | 0959091 | 11/1999 |
| EP | 1068855 | 1/2001 |
| WO | WO 95/24887 | 9/1995 |
| WO | WO 98/17705 | 4/1998 |
| WO | WO 98/47470 | 10/1998 |

\* cited by examiner

*Primary Examiner*—P. Hampton Hightower
(74) *Attorney, Agent, or Firm*—Thomas W. Barnes, III

(57) ABSTRACT

Polymerized fatty acid-based polyamides may be combined with low polarity and high polarity co-solvents to produce homogeneous water-in-oil emulsions. These emulsions have the appearance of white or translucent creams, with stiffness ranging from soft and greasy, to hard and able to support weight. These emulsions are stable in the presence or absence of surfactant, and are formed easily by mixing components with heat and then cooling. These emulsions are useful in applications favoring an oil base, such as skin creams and cosmetics with emulsions of low stiffness, and car polish with emulsions of greater stiffness.

20 Claims, No Drawings

AQUEOUS SUSPENSIONS CONTAINING POLYMERIZED FATTY ACID-BASED POLYAMIDES

BACKGROUND OF THE INVENTION

1. Field of the Invention

The field of the invention is aqueous polyamide suspensions.

2. Description of the Related Art

Polyamide resins are typically synthesized by reacting dicarboxylic acid-containing compounds with diamine-containing compounds. This reaction produces repeating hydrocarbon subunits connected to each other through amide bond linkages. Nylon is one type of particularly well-known polyamide, although there are many other types of polyamide compounds possessing various strength, flexibility, and solubility properties, due largely to the lengths of the hydrocarbon portions of the reacting species.

One particularly useful type of polyamide is made from polymerized fatty acid, also referred to as dimer acid. These polyamides may be referred to as polymerized fatty acid-based polyamides, or dimer acid-based polyamides. Sometimes these polyamides are also referred to polymerized fatty acid-containing polyamides, however, it should be noted that polymerized fatty acid per se is not present to any great extent in these polyamides, and that the term "polymerized fatty acid-containing" is really a shorthand expression that denotes that the polyamides were prepared from polymerized fatty acid. Regardless of their name, in structural terms these polyamides contain longer hydrocarbon regions than are found in nylons, and may be terminated at each end by organic functional moieties such as amide and ester groups. Generally, the molecular structures of polymerized fatty acid-based polyamides impart to these resins properties of strength and flexibility, making them particularly useful in formulations for protective coatings and gelling agents. Indeed, articles of commerce such as candles, air fresheners, and cable protectants can be manufactured with the use of such resins.

Because of the prominence of the hydrocarbon regions in typical polymerized fatty acid-based polyamides, such resins are often combined with low-polarity components, such as mineral oils and cosmetic-grade esters. However, a few polyamides have been formulated to be compatible with water, as described in the following representative U.S. Patents.

U.S. Pat. No. 5,324,812 discloses preparative procedures and compositions for a water-soluble polyamide resin derived from polyoxyalkylene diamine. This Patent mentioned that the polyamide disclosed therein may be useful in various products including lubricants, mold release agents, disposable items (such as plastic containers), water thickeners, encapsulants, temporary protective coatings, and in particular, hot melt adhesive formulations.

U.S. Pat. No. 5,466,734 discloses preparative procedures and compositions for a cold seal release lacquer comprising polyamide block copolymer, amide wax, alkanolamine, water, and optionally surfactant, wherein the polyamide block copolymer has an acid number of 30–45. Cold seal release lacquers are used as protective coatings for film wrapping of consumable products.

U.S. Pat. Nos. 5,886,135 and 5,948,880 disclose compositions to make dispersions from polyamide, water, and either surfactant or thickener, wherein the surfactant is a mixture of nonionic and anionic surfactants, while the thickener is selected from, e.g., urethane thickeners and polyether thickeners. These Patents disclose preparative procedures wherein an organic phase (comprising organic solvent, polyamide resin, surfactant, and inorganic base) is combined with an aqueous phase (comprising water and acid), after which much of the organic solvent is removed. These polyamides are purportedly useful as coatings and adhesives.

U.S. Pat. No. 5,962,629 discloses a composition for an aqueous dispersion that contains water and polyamide terminated by aminoalkylpiperazyl groups. Related U.S. Pat. No. 5,998,508 discloses a composition for a curable epoxy resin comprising the aqueous dispersion of the '629 Patent in combination with an epoxy resin. Related U.S. Pat. No. 6,013,757 discloses a cord substrate impregnated with the curable epoxy resin of the '508 Patent.

U.S. Pat. No. 6,077,900 discloses a dispersion containing polymerized fatty acid-based polyamide, amide-free polymeric component, and surfactant, and states that this dispersion may be formed by combining the listed components in the presence of water and an organic solvent, where the organic solvent must have some solubility in water. This Patent further discloses that the pH of the organic and aqueous phases needs to be adjusted so as to promote formation of an oil-in-water dispersion when combined, without polyamide coagulation. The '900 Patent also states that these dispersions are useful in various products such as printing inks and general coating material.

U.S. Pat. No. 6,103,809 discloses a composition for an adhesive that contains water-sensitive and/or water-dispersible polyamides. The products may also include wax.

U.S. Pat. No. 6,165,971 discloses an aqueous composition for a cosmetic, comprising a specifically terminated amide-terminated polyamide, and a component selected from surfactant and polyglycoside.

The present invention provides improvements in the art of water-soluble polyamides, and provides other related advantages as disclosed below.

BRIEF SUMMARY OF THE INVENTION

In one aspect, the present invention provides a composition comprising polymerized fatty acid-based polyamide, organic solvent, and water, wherein the polyamide is a gellant for the organic solvent. In one embodiment, the composition has an aqueous continuous phase and an organic discontinuous phase. In another embodiment, the composition has an organic continuous phase and an aqueous discontinuous phase. For example, the present invention provides a compositions comprising (a) a discontinuous aqueous phase; (b) a continuous organic phase comprising an organic solvent that is a liquid at room temperature, and is either insoluble in water or is soluble in water to an extent of less than about 1.0 gram organic solvent per 100 grams water at 25° C.; and (c) a polyamide gellant selected from ester-terminated polyamide or amide-terminated polyamide.

In the compositions, the polyamide gellant may be an ester-terminated polyamide of formula (1) as defined herein:

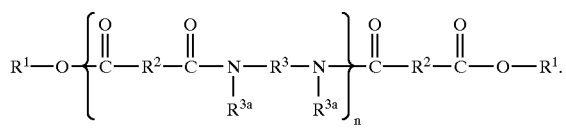

(1)

Alternatively, the polyamide gellant may be a tertiary amide-terminated polyamide of formula (2) as defined herein:

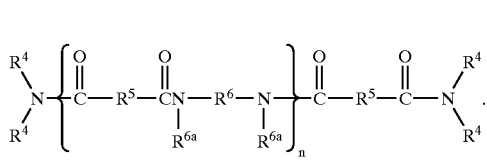

(2)

In various embodiments of the invention, the organic solvent may be described by one, or any two, or all three of the following criteria: the organic solvent is immiscible with water; the organic solvent has at least eight carbons; the organic solvent comprises a hydrocarbon, i.e., the organic solvent either is hydrocarbon or a hydrocarbon solvent is one of the components of the organic solvent. In various embodiments of the invention, the composition may be described by one, or any two, or all three of the following criteria: the polyamide is 1–30% of the total weight of the composition; the organic solvent is 10–70% of the total weight of the composition; the water is 20–90% of the total weight of the composition. Various optional components may be present in the composition, including wax, surfactant, buffer, silicon oil and bactericide.

In a related aspect, the present invention provides a composition that contains polymerized fatty acid-based polyamide, organic solvent, and water, wherein: (a) the polymerized fatty acid-based polyamide is selected from ester-terminated polyamide and tertiary amide-terminated polyamide; and (b) the organic solvent is a liquid at room temperature, and is either insoluble in water or is soluble in water to an extent of less than about 1.0 gram organic solvent per 100 grams water at 25° C. In a different related aspect, the present invention provides a composition that includes: (a) a dispersed aqueous phase; (b) a continuous organic phase comprising an organic solvent that is a liquid at room temperature, and is either insoluble in water or is soluble in water to an extent of less than about 1.0 gram organic solvent per 100 grams water, at 25° C.; and (c) polymerized fatty acid-based polyamide selected from ester-terminated polyamide or amide-terminated polyamide. In yet another related aspect, the present invention provides a composition that includes polymerized fatty acid-based polyamide, organic solvent, wax and water. Optionally, but preferably, the polymerized fatty acid-based polyamide is not water soluble, e.g., it has an acid number of less than 25 and an amine number of less than 25. In yet another related aspect, the present invention provides a composition that includes a dispersed aqueous phase; a continuous organic phase comprising an organic solvent that is a liquid at room temperature; wax; and polymerized fatty acid-based polyamide. Optionally, the wax is a hydrocarbon wax.

In another aspect, the present invention provides a process for preparing a water-in-oil emulsion. The process includes heating components that include organic solvent, water, and polymerized fatty acid-based polyamide to a provide a fluid mixture; stirring the fluid mixture to provide a macroscopically homogenous mixture; and cooling the homogeneous mixture to room temperature to provide an emulsion. In one optional embodiment, this process includes the ordered steps of: (a) forming an initial mixture wherein an organic solvent is combined with polymerized fatty acid-based polyamide with stirring; (b) heating the initial mixture to provide a single fluid phase in which organic solvent and polyamide are distributed evenly throughout the phase; and (c) adding water with stirring to the single fluid phase (b) to provide an emulsion. In another optional embodiment, this process includes the ordered steps of: (a) combining organic solvent, water, and polymerized fatty acid-based polyamide, with stirring, to provide an initial mixture; (b) heating the initial mixture to about 90–120° C. to form a fluid phase in which components are distributed evenly throughout the phase; (c) allowing the mixture formed in (b) to cool to room temperature.

In another aspect, the present invention provides a cosmetic or other personal care product that includes a water-in-oil emulsion as described herein and/or made by a process provided herein.

In another aspect, the present invention provides a composition that includes: (a) a dispersed aqueous phase; (b) a continuous organic phase comprising an organic solvent that is a liquid at room temperature; (c) wax; and (d) polymerized fatty acid-based polyamide. The wax may be, for example, a hydrocarbon wax. In one aspect, the composition does not contain any surfactant, while in another embodiment the composition contains only a small amount of surfactant, e.g., less than 1 wt %. In a related aspect, the present invention provides a method of polishing the surface of a substrate, where the method includes (a) applying a composition of the present invention as described herein to a surface of a substrate; and (b) wiping the composition off of the substrate to provide a polished surface.

These and related aspects of the present invention are set forth more fully below.

DETAILED DESCRIPTION OF THE INVENTION

The present invention is directed to the use of polymerized fatty acid-based polyamide gellants, such as ester-terminated polyamides (ETPA) and tertiary amide-terminated polyamides (ATPA), in the formation of macroscopically homogeneous suspensions that also include water and organic solvent. In one aspect, the polyamide gellant and a gelled organic solvent are the continuous phase of the suspension, with an aqueous phase as the discontinuous phase. In another aspect, the polyamide gellant and gelled organic solvent are the discontinuous phase and the aqueous phase is the continuous phase. These suspensions may be used as bases for such consumer products as cosmetics, insect repellents, lubricants, sunscreens, furniture polish, car polish, shoe polish, etc.

As used herein, the term suspension refers to compositions that are homogeneous on a macroscopic scale but heterogeneous on a microscopic scale. That is, the suspension is at least bi-phasic in that it contains a continuous phase and at least one discontinuous phase. As discussed in further detail below, the suspension may contain more than one compositionally distinct discontinuous phase. The terms "emulsion" and "dispersion" refer to two types of suspension. Both emulsions and dispersions contain distinct water and organic phases. When water is the discontinuous phase and the organic compound(s) is the continuous phase, this is referred to as a water-in-oil emulsion or dispersion. When the organic compound(s) is the discontinuous phase and water is the continuous phase, this is referred to as an oil-in-water emulsion or dispersion. In an emulsion, the discontinuous phase is a liquid, while in a dispersion the discontinuous phase is a solid. Thus, as used herein, the term "emulsion" is defined as a mixture having the macroscopic appearance of a single distinct phase, created from a mixture of two immiscible phases. The term "homogeneous" is used to describe an emulsion wherein droplets of liquid are distributed evenly through a continuous phase, where the continuous phase may be a solid, liquid or a gel. The term "homogeneous" may also be used to describe a dispersion wherein solid or gelled particulates are evenly distributed through a continuous phase, where the continuous phase may be a solid, liquid or a gel. As used herein and throughout the description of the invention, the term "a" refers to one or more of the indicated items.

Thus, in one aspect, the present invention provides a water-in-oil emulsion. In another aspect, the present invention provides an oil-in-water suspension, where the oil may be liquid or solid or gel. In preferred aspects, as discussed below, the present invention provides emulsions possessing cream-like consistencies.

The suspensions of the present invention contain at least three components, namely, water, water-immiscible solvent, and polyamide. In certain embodiments of the invention, the suspension also contains a surfactant. In certain embodiments of the invention, the suspension also contains wax. Each of these components, as well as other components, is described below. The suspensions may contain other optional ingredients.

As used herein, the term "polymerized fatty acid-based polyamides" refers to polyamides that are prepared, in part, from polymerized fatty acid or reactive equivalents thereof. The polyamides preferably have both low acid number and low amine number. As used herein, the term "low acid number" refers to an acid number of less than 25, preferably less than 20, more preferably less than 15, still more preferably less than 10, and yet still more preferably less than 5. As used herein, "low amine number" refers to an amine number of less than 25, preferably less than 20, more preferably less than 15, still more preferably less than 10, and yet still more preferably less than 5.

The polyamides useful in the present invention are gellants for the organic solvent used in the inventive suspension. Whether a polyamide is a gellant for a particular organic solvent can be determined by the following simple test. A standard test tube (e.g., one having a length of about 5 inches and an inner diameter of about 0.5 inches) is charged with 0.8 g polyamide and 3.2 grams of organic solvent. The mixture is heated to provide a homogeneous mixture. Maintaining the mixture at a temperature of about 120° C. for a time of about 5 hours is typically sufficient to achieve a homogeneous mixture. Some stirring and/or shaking of the mixture may be used to hasten the formation of homogeneous state. After the homogenous state has been achieved at elevated temperature, the mixture is allowed to cool to room temperature, i.e., about 25° C. and evaluated for appearance the physical properties. A polyamide is a gelling agent for the organic solvent if the cooled mixture is homogeneous and appears either clear or hazy. In addition, upon inversion of the test tube, if the cooled mixture remains as a plug at the bottom of the tube, rather than running down the side or falling out of the tube, then the polyamide is a gelling agent for the organic solvent. In one aspect of the invention, a polyamide is a suitable gellant if it will gel at least one of 2-ethylhexyl acetate or isopropyl myristate. In another aspect, a polyamide is a suitable gellant if it will gel a hydrocarbon, e.g., mineral oil or petroleum ether.

In one aspect, the polyamide gellant is an ester-terminated polyamide of the general formula

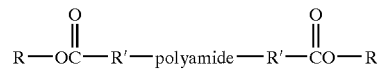

having a polyamide mid-portion flanked by two ester groups. As described in further detail below, such polyamides will typically be prepared by reacting together dicarboxylic acid and diamine, and/or reactive equivalents thereof, so as to form a polyamide mid-portion, where this reaction will be conducted in the presence of monohydric compound, i.e., alcohol of the formula R—OH, where this monofunctional material will cap, or terminate, the polyamide structure and thereby provide ester groups at either end of the polyamide chain. The polyamide mid-portion will typically have 2–10 amide groups. The R and R' groups will typically be, and in one aspect are, hydrocarbon groups.

In one aspect, the polyamide is an ester-terminated polyamide referred to herein as ETPA. The general molecular structure of an ETPA is as shown in formula (1):

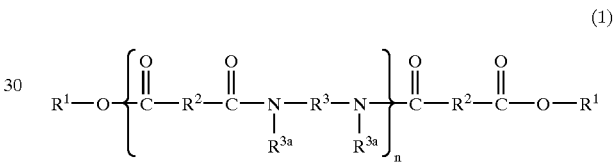

(1)

wherein n designates a number of repeating units such that ester groups constitute from 10% to 50% of the total of the ester and amide groups; $R^1$ at each occurrence is independently selected from an alkyl or alkenyl group containing at least 2 carbon atoms, preferably at least 4 carbon atoms; $R^2$ at each occurrence is independently selected from a $C_{4-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen. For convenience, $R^1$, $R^2$, $R^3$ etc. will be referred to herein as "groups", however they could equally well be referred to as radicals ($R^1$) and diradicals ($R^2$ and $R^3$).

As may be seen from formula (1), the ester-terminated polyamides of the invention have ester groups, i.e., —C(=O)O— groups (which may equally well be written as —OC(=O)— groups) at both ends of a series of amide groups, i.e., —N($R^{3a}$)C(=O)— groups (which may equally well be written as —C(=O)N($R^{3a}$)— groups). The letter "n" designates the number of repeating units present in a molecule of ETPA, and is an integer greater than 0. According to the invention, n may be 1, in which case the ETPA contains equal amounts of ester and amide groups, i.e., the ester groups constitute 50% of the total of the ester and amide groups in the ETPA molecule. Preferably, the ETPA molecules are of relatively low molecular weight, so that n is preferably 1 to about 10, and more preferably is 1 to about 5. Because the ETPA molecules have such a low molecular weight, they could equally well be referred to as ester-terminated oligoamides. In any event, viewed another way, the ester groups constitute about 10% to about 50%, preferably about 15% to about 40%, and more preferably about 20% to about 35% of the total of the ester and amide groups. The invention is also directed to a mixture of ETPA molecules having various n values.

The $R^1$ group in formula (1) is an alkyl or alkenyl group that contains at least 2, and preferably at least 4 carbon atoms. Alkyl groups are preferred, however alkenyl groups having 1–3, and preferably 1 site of unsaturation are also suitable. When ETPA molecules are made wherein $R^1$ has 4 or less carbon atoms, the ETPA molecule is a very poor gellant for pure hydrocarbon, particularly pure aliphatic hydrocarbon, and accordingly $R^1$ groups having 2 or 3 carbon atoms are less preferred in the preparation of suspensions of the present invention. When the number of carbon atoms in the $R^1$ group is increased above 4, and preferably is increased to about 10 or more carbon atoms, more preferably at least about 12 carbon atoms, then the ETPA molecule and blends thereof are an excellent gellant for aliphatic hydrocarbon. The upper range for the number of carbon atoms in the $R^1$ group is not particularly critical, however preferably the $R^1$ group has less than or equal to about 24 carbon atoms, and more preferably has less than or equal to 22 carbon atoms. $R^1$ groups having about 16–22 carbon atoms are highly preferred. The identity of $R^1$ at any occurrence is independent of the identity of $R^1$ at any other occurrence.

The $R^2$ group in formula (1) is a hydrocarbon containing 4 to 42 carbon atoms. A preferred $R^2$ group contains 30–42 carbon atoms (i.e., is a $C_{30-42}$ group), and in fact at least 50% of the $R^2$ groups in an ETPA molecule or mixture of ETPA molecules have 30–42 carbon atoms. Such $R^2$ groups are readily introduced into an ETPA molecule when the molecule is prepared from polymerized fatty acid, also known as dimer acid. Polymerized fatty acid is typically a mixture of structures, where individual dimer acids may be saturated, unsaturated, cyclic, acyclic, etc. Thus, a detailed characterization of the structure of the $R^2$ groups is not readily available. However, good discussions of fatty acid polymerization may be found in, e.g., U.S. Pat. No. 3,157,681 and *Naval Stores—Production, Chemistry and Utilization*, D. F. Zinkel and J. Russel (eds.), Pulp. Chem. Assoc. Inc., 1989, Chapter 23.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in the invention. While tall oil fatty acid is a preferred source of long-chain fatty acid, the polymerized fatty acid may alternatively be prepared by polymerization of unsaturated fatty acids from other sources, e.g., soybeans or canola. The $R^2$ group containing 30–42 carbon atoms may thus be described as having the structure of dimer or trimer acid, after removal of the carboxylic acid groups (as seen below, the carboxylic acid groups of dimer acid can react to form the amide and/or ester groups of the ETPA molecules).

While the ETPA molecules contain at least 50% $C_{30-42}$ groups as the $R^2$ group, preferably the total of the $R^2$ groups consist of at least 75% $C_{30-42}$ groups, and more preferably consist of at least 90% $C_{30-42}$ groups. An ETPA molecule, and mixtures of ETPA molecules, wherein $R^2$ is entirely $C_{30-42}$ is a preferred ETPA for preparation of suspensions according to the present invention.

ETPA molecules may contain $R^2$ groups having less than 30 carbon atoms. For example, an ETPA molecule may contain one or more $R^2$ groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^2$ may be aliphatic or aromatic. When present, these lower carbon-number $R^2$ groups are preferably formed entirely of carbon and hydrogen, i.e., are hydrocarbon groups. Such lower carbon-number $R^2$ groups preferably constitute less than 50% of the $R_2$ groups; however, when present, constitute about 1% to about 50%, and preferably about 5% to about 35% of the total of the $R^2$ groups. The identity of $R^2$ at each occurrence is independent of the identity of $R^2$ at any other occurrence.

The —N($R^{3a}$)—$R^3$—N($R^{3a}$)— group in formula (1) links two carbonyl (C=O) groups. In a preferred ETPA, all of the $R^{3a}$ groups are hydrogen, so that $R^3$ alone joins the two nitrogen atoms shown in the formula —N($R^{3a}$)—$R^3$—N($R^{3a}$)—. In this case, the $R^3$ group contains at least two carbon atoms, and optionally oxygen and/or nitrogen atoms, in addition to hydrogen atoms necessary to complete otherwise unfilled vacancies of the carbon, oxygen and nitrogen atoms. In a preferred embodiment, $R^3$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^3$ group may contain aliphatic or aromatic structures. The identities of $R^3$ and $R^{3a}$ at each occurrence are independent of their identities at any other occurrence. However, the two $R^{3a}$ groups may join together so as to form a cyclic structure in combination with $R^3$ and the two nitrogens to which the $R^3$ group is attached.

The $R^3$ groups may contain oxygen and/or nitrogen in addition to carbon and hydrogen atoms. A typical oxygen atom-containing $R^3$ group is a polyalkylene oxide, i.e., a group having alternating alkylene groups and oxygen atoms. Indeed, the oxygenation in a $R^3$ group is preferably present as an ether group. Representative polyalkylene oxides include, without limitation, polyethylene oxide, polypropylene oxide and copolymers (either random or block) of ethylene oxide and propylene oxide. While some of the $R^3$ groups may contain oxygen (i.e., at least about 1%), preferably a minor number (i.e., less than 50%) of the $R^3$ groups contain oxygen, and more preferably less than about 20% of the $R^3$ groups contain oxygen. The presence of oxygen-containing $R^3$ groups tend to lower the softening point of the ETPA.

When present, the nitrogen atoms in an $R^3$ group are preferably present as secondary or tertiary amines. A typical nitrogen atom-containing $R^3$ group having secondary amine groups is a polyalkylene amine, i.e., a group containing alternating alkylene groups and amine groups, and sometimes referred to as a polyalkylene polyamine. The alkylene group is preferably a lower alkylene group, e.g., methylene, ethylene, (i.e., —$CH_2CH_2$—), propylene etc. A typical polyalkylene amine may be represented by the formula —NH—($CH_2CH_2NH$)$_m$$CH_2CH_2$—NH— wherein m is an integer from 1 to about 5.

However, the nitrogen atoms in the nitrogen-containing $R^3$ group may alternatively (or additionally) be present as tertiary nitrogen atoms, e.g., they may be present in a heterocycle of the formula:

wherein $R_c$ is a $C_{1-3}$ alkyl group.

In the above-described nitrogen atom-containing $R^3$ groups, $R^{3a}$ was hydrogen. However, $R^{3a}$ need not be limited to hydrogen. In fact, $R^{3a}$ may be a $C_{1-10}$ alkyl group, preferably a $C_{1-5}$ alkyl group, and more preferably a $C_{1-3}$ alkyl group. In addition, $R^3$ and $R^{3a}$, or two $R^{3a}$ groups, may together form a heterocyclic structure, e.g., a piperazine structure such as

In this case, the two $R^{3a}$ groups may be seen as joining together to form an ethylene bridge between the two nitrogen atoms, while $R^3$ is also an ethylene bridge.

A resin comprising the EPTA molecules of formula (1) may also comprise, for example, by-products that are formed during the ETPA-forming reaction. While the ETPA molecules of formula (1) may be purified from such by-products using, e.g., chromatography or distillation, the either minimal in amount or impart desirable properties to the resin, and thus need not be separated from the ETPA molecules of formula (1).

The process of synthesizing ETPA, as well as the general chemical properties of ETPA, are described in U.S. Pat. No. 5,783,657, where this Patent is incorporated herein by reference in its entirety. A suitable EPTA resin is commercially available as UNICLEAR™ 100 ester-terminated polyamide (Arizona Chemical, Jacksonville, Fla.).

In one aspect, the polyamide gellant is a tertiary amide-terminated polyamide of the general formula

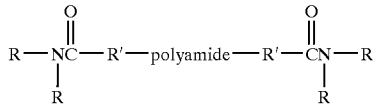

having a polyamide mid-portion flanked by two tertiary amide groups. As described in further detail below, such polyamides will typically be prepared by reacting together dicarboxylic acid and diamine, and/or reactive equivalents thereof, so as to form a polyamide mid-portion, where this reaction will be conducted in the presence of secondary amine compound, i.e., amine of the formula $R_2NH$, where this monofunctional material will cap, or terminate, the polyamide structure and thereby provide tertiary amide groups at either end of the polyamide chain.

In one aspect of the invention, the polyamide is a tertiary amide terminated polyamide referred to herein as ATPA. The general molecular structure of an ATPA is shown in formula (2):

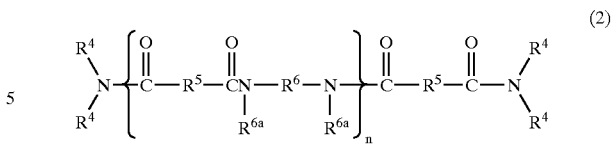

In formula (2), n designates a number of repeating units such that terminal (i.e., $R^4$-containing) amide groups constitute from 10% to 50% of the total of the amide groups shown in formula (2); $R^4$ at each occurrence is independently selected from a $C_{1-22}$ hydrocarbon group; $R^5$ at each occurrence is independently selected from a $C_{2-42}$ hydrocarbon group with the proviso that at least 50% of the $R^5$ groups have 30–42 carbon atoms; $R^6$ at each occurrence is independently selected from an organic group containing at least two carbon atoms in addition to hydrogen atoms, and optionally containing one or more oxygen and nitrogen atoms; and $R^{6a}$ at each occurrence is independently selected from hydrogen, $C_{1-10}$ alkyl and a direct bond to $R^6$ or another $R^{6a}$ such that the N atom to which $R^6$ and $R^{6a}$ are both bonded is part of a heterocyclic structure defined in part by $R^{6a}$—N—$R^6$, such that at least 50% of the $R^{6a}$ groups are hydrogen.

In one aspect, the ATPA resin comprises diamide having formula (2) wherein n=0, such that the ratio of terminal amide groups to the sum of amide groups in the total of the molecules that comprise the resin of formula (2) is from 0.1 to 0.7. Preferably, the resin composition is at reaction equilibrium.

As may be seen from formula (2), the ATPA resins have terminal amide groups of the formula —C(=O)N($R^4$)($R^4$) at both ends of a series of amide groups. These terminal amide groups are formed from secondary amines (since $R^4$ is an organic group and is not hydrogen), and therefore the terminal amide groups in formula (2) are properly referred to as tertiary amide groups. Accordingly, the ATPA resins may be referred to as tertiary amide-terminated polyamides.

The letter "n" in formula (2) designates the number of repeating units present in a molecule of ATPA, and is an integer greater than 0. The designator n may be 1, in which case the ATPA contains equal numbers of terminal amide and non-terminal amide groups, i.e., the terminal amide groups constitute 50% of the total of the amide groups in the ATPA molecule. The preferred ATPA resins are of relatively low molecular weight, so that n is preferably 1 to about 10, and more preferably is 1 to about 5. Because the ATPA molecules have such a low molecular weight, they could equally well be referred to as tertiary amide-terminated oligoamides. In any event, viewed another way, the terminal amide groups constitute about 10% to about 50%, preferably about 15% to about 40%, and more preferably about 20% to about 35% of the total of the amide groups. A preferred ATPA resin includes a mixture of ATPA molecules of formula (2) having various n values. The ATPA resin has a weight average molecular weight of less than about 10,000, and typically less than about 5,000, but more than 500, typically more than 1,000, when measured by gel permeation chromatography using polystyrene calibration standards.

The $R^4$ group in formula (2) is a hydrocarbon group, and preferably is an alkyl or alkenyl group that contains at least 1, typically at least 4, and preferably more than 4 carbon atoms, e.g., 8, 10, 12, 14, 16, 18, 20, 22, 30, 40, or 50 carbon atoms. Alkyl groups are preferred, however alkenyl groups having 1–3, and preferably 1 site of unsaturation are also suitable. The upper range for the number of carbon atoms in the $R^4$ group is not particularly critical, however preferably the $R^4$ group has less than or equal to about 22 carbon atoms. $R^4$ groups having about 16–22 carbon atoms are highly preferred. The identity of $R^4$ at any occurrence is independent of the identity of $R^4$ at any other occurrence.

The $R^5$ group in formula (2) is suitably a hydrocarbon containing 2 to 42 carbon atoms, and preferably contains 4 to 42 carbon atoms. A more preferred $R^5$ group contains 30–42 carbon atoms (i.e., is a $C_{30-42}$ group), and at least 50% of the $R^5$ groups in an ATPA resin preferably have 30–42 carbon atoms. Such $R^5$ groups are readily introduced into an ATPA when the resin is prepared from polymerized fatty acid, also known as dimer acid. Polymerized fatty acid is typically a mixture of structures, where individual dimer acids may be saturated, unsaturated, cyclic, acyclic, etc. Thus, a detailed characterization of the structure of the $R^5$ groups is not readily available. However, good discussions of fatty acid polymerization may be found in, for example, U.S. Pat. No. 3,157,681 and *Naval Stores—Production, Chemistry and Utilization*, D. F. Zinkel and J. Russel (eds.), Pulp. Chem. Assoc. Inc., 1989, Chapter 23. While the preferred ATPA resins contain at least 50% $C_{30-42}$ groups as the $R^5$ group, more preferably the total of the $R^5$ groups consist of at least 75% $C_{30-42}$ groups, and still more preferably consist of at least 90% $C_{30-42}$ groups. ATPA resins of formula (2) wherein $R^5$ is entirely $C_{30-42}$ are preferred components of the invention.

However, ATPA resins may also contain $R^5$ groups having less than 30 carbon atoms. For example, an ATPA resin may contain one or more $R^5$ groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^5$ may be aliphatic or aromatic. When present, these lower carbon-number $R^5$ groups are preferably formed entirely of carbon and hydrogen, i.e., are hydrocarbyl groups. Such lower carbon-number $R^5$ groups preferably constitute less than 50% of the $R^5$ groups; however, when present, constitute about 1% to about 50%, and preferably about 5% to about 35% of the total of the $R^5$ groups. The identity of $R^5$ at each occurrence is independent of the identity of $R^5$ at any other occurrence. The —N($R^{6a}$)—$R^6$—N($R^{6a}$)— group in formula (2) links two carbonyl (C=O) groups. In a preferred embodiment of the invention, all of the $R^{6a}$ groups in an ATPA resin are hydrogen, so that $R^6$ alone joins the two nitrogen atoms shown in the formula —N($R^{6a}$)—$R^6$—N($R^{6a}$)—. In this case, the $R^6$ group contains at least two carbon atoms, and optionally oxygen and/or nitrogen atoms, in addition to any hydrogen atoms that are necessary to complete otherwise unfilled valencies of the carbon, oxygen and nitrogen atoms. In one embodiment, $R^6$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^6$ may contain aliphatic or aromatic structures. The identities of $R^6$ and $R^{6a}$ at each occurrence are independent of their identities at any other occurrence.

The $R^6$ groups may contain oxygen and/or nitrogen in addition to carbon and hydrogen atoms. A typical oxygen atom-containing $R^6$ group is a polyalkylene oxide, i.e., a group having alternating alkylene groups and oxygen atoms. Indeed, the oxygenation in a $R^6$ group is preferably present as an ether group. Representative polyalkylene oxides include, without limitation, polyethylene oxide, polypropylene oxide and copolymers (either random, alternating or block) of ethylene oxide and propylene oxide. While some of the $R^6$ groups may contain oxygen (at least about 1%), preferably a minor number (less than 50%) of the $R^6$ groups contain oxygen, and more preferably less than about 20% of the $R^6$ groups contain oxygen. The presence of oxygen-containing $R^6$ groups tends to lower the softening point of the ATPA resin.

When present, the nitrogen atoms in an $R^6$ group are preferably present as secondary or tertiary amines. A typical nitrogen-containing $R^6$ group having secondary amine groups is a polyalkylene amine, i.e., a group containing alternating alkylene groups and amine groups, which is sometimes referred to as a polyalkylene polyamine. The alkylene group is preferably a lower alkylene group, e.g., methylene, ethylene, (i.e., —$CH_2CH_2$—), propylene, etc. A typical polyalkylene amine may be represented by the formula —NH—($CH_2CH_2NH$)$_m$$CH_2CH_2$—NH— wherein m is an integer from 1 to about 5.

However, the nitrogen atoms in the nitrogen-containing $R^6$ group may alternatively (or additionally) be present as tertiary nitrogen atoms, e.g., they may be present in a heterocycle of the formula:

wherein $R_c$ is a $C_{1-3}$ alkylene group. In the above-described nitrogen-containing $R^6$ groups, $R^{6a}$ was hydrogen. However, $R^{6a}$ is not limited to hydrogen. In fact, $R^{6a}$ may be a $C_{1-10}$alkyl group, preferably a $C_{1-5}$alkyl group, and more preferably a $C_{1-3}$alkyl group. In addition, $R^6$ and $R^{6a}$, or two $R^{6a}$ groups, may together form a heterocyclic structure, e.g., a piperazine structure such as

In this case, the two $R^{6a}$ groups may be seen as joining together to form an ethylene bridge between the two nitrogen atoms, while $R^6$ is also an ethylene bridge.

The ATPA resin typically includes a mixture of ATPA molecules of formula (2) in addition to, for example, by-products that are formed during the ATPA-forming reaction. While the ATPA molecules of formula (2) may be purified from such by-products using, for example, chromatography or distillation, the by-products are typically either minimal in amount or impart desirable properties to the resin when the resin functions as a gelling agent, and thus need not be separated from the molecules of formula (2) in order for a suitable ATPA resin to be formed.

The process of synthesizing ATPA, as well as the general chemical properties of ATPA, are described in U.S. Pat. No. 6,268,466, where this Patent is incorporated herein by reference in its entirety. A suitable ATPA resin is also commercially available as SYLVACLEAR A-200™ tertiary amide-terminated polyamide (Arizona Chemical, Jacksonville, Fla., U.S.A.).

In another aspect, the polyamide gellant is prepared from a mixture of nonfunctional capping agents. For example, a mixture of secondary amine compound, i.e., amine of the formula $R_2NH$ where this monofunctional material will cap, or terminate, the polyamide structure and thereby provide a tertiary amide group at an end of the polyamide chain, and a primary alcohol, i.e., an alcohol of the formula R—OH, where this monofunctional material will also cap, or terminate, the polyamide structure and thereby provide an ester group at an end of the polyamide chain. When a mixture of first and second monofunctional capping agents are employed, the product resin will be a mixture of polyamides, where the mixture consists of polyamide capped only with the first capping agent, polyamide capped only with the second capping agent, and polyamide capped on one end by the first capping agent and on the other end by the second capping agent.

The suspensions of the present invention also include an organic solvent. Herein, an "organic solvent" is defined as a substance that is a liquid when in neat (i.e., pure) form at room temperature (25° C.) and contains at least one carbon in its molecular structure. The organic solvent is preferably immiscible in water so that when the suspension is formed, the organic solvent does not migrate from the phase containing the gellant and organic solvent and into the aqueous phase. Alternatively, the organic solvent may have a very slight miscibility with water, e.g., the organic solvent is miscible with water at a concentration of less than about 1.0 grams organic solvent per 100 grams water at 25° C. In other words, an organic solvent that is not miscible with water will form two phases when more than about 1.0 grams of organic solvent are combined with 100 grams of water at 25° C. As discussed in detail below, exemplary organic solvents according to the present invention include hydrocarbons and ester-containing solvents.

A preferred organic solvent is a hydrocarbon, where the hydrocarbon may be aliphatic or aromatic. A preferred hydrocarbon is an oil, where mineral oil is a preferred oil. Mineral oils useful in the invention include, but are not limited to, transformer oil, spindle oil, cable insulating oil and machine oil. In one embodiment, the mineral oil is food grade mineral oil. Examples of suitable, commercially available mineral oils include SONNEBORN™ and CARNATION™ white oils from Witco Corp. (Greenwich, Conn.); and DRAKEOL™ and PENETECK™ white mineral oils from Penreco (Karns City, Pa.).

Other hydrocarbons that may be used in the invention include relatively lower molecular weight hydrocarbons including linear saturated hydrocarbons such as tetradecane, hexadecane, octadecane, etc. Cyclic hydrocarbons such as decahydronaphthalene (DECALIN™), fuel grade hydrocarbons, branched chain hydrocarbons such as PERMETHYL™ from Permethyl Corp. and ISOPAR™ from Exxon Corp. (Houston, Tex.); ISOPAR™ K and ISOPAR™ H petroleum ether from Exxon Corp. (Houston, Tex.); and hydrocarbon mixtures such as product PD-23™ from Witco Corp. (Greenwich, Conn.) may also be used in preparing suspensions of the invention. Such hydrocarbons, particularly saturated hydrocarbon oils, are a preferred solvent for preparing a suspension, and particularly an emulsion of the invention. Aromatic hydrocarbons, e.g., toluene or xylene, may also function as the solvent in a suspension of the invention. One preferred embodiment of an emulsion of the present invention employs mineral oil and/or petroleum ether as the organic solvent.

In another aspect the organic solvent is an ester-containing compound. An ester-containing compound will include the structural formula —C(=O)—O—, and preferably includes the structural formula —C(=O)—O—$R^7$ where $R^7$ is selected from $C_{1-22}$ hydrocarbyl groups. As used herein, a hydrocarbyl group is formed exclusively from carbon and hydrogen. Such ester-containing compounds may be monofunctional esters (i.e., have a single ester moiety) or may be polyfunctional (i.e., have more than one ester group). Suitable esters include, but are not limited to, the reaction products of $C_{1-24}$ monoalcohols (i.e., a monohydric organic compound having from 1 to 24 carbons) with $C_{1-24}$ monocarboxylic acids (i.e., an organic compound having from 1 to 24 carbons and a single carboxylic acid group), where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, and triacontanyl stearate. Other suitable esters include glycerol and propylene glycol esters of fatty acids, such as the so-called polyglycerol fatty acid esters and triglycerides.

In addition to polyamide and organic solvent, the suspensions of the present invention include water. For reasons of cost and availability, the water is preferably tap-grade water. However, purified water, e.g., doubly distilled water or spring water, may be employed. The water typically has a pH of about 7.0, that is, of about 6.3 to about 7.8. It is possible to add acid or base to the water, however that is not necessary in the practice of the present invention, and in a preferred embodiment of the invention neither acid nor base has been added to the water. The polyamides used in the present invention preferably do not have high acid numbers or high amine numbers, where these high acid or amine numbers would reflect a high content of acid or amine groups, respectively, that might be placed into ionized form by pH adjustment so as to aid in the solubility of the polyamide in an aqueous environment. In fact, in one aspect, the polyamides of the present invention are not soluble to any great extent in water at any pH, i.e., less than 5 g, and preferably less than 1 g, of polyamide dissolves in 100 g of water at 25° C.

The polyamides of the present invention preferably have an acid number of less than 25, and an amine number of less than 25.

In one aspect that provides a suspension of the present invention, the organic solvent is 1–99%, the polyamide is 1–40% and the water is 1–99% of the total weight of the composition. In another aspect, the organic solvent is 10–60%, the polyamide is 5–30% and the composition. In another aspect, the organic solvent is 20–50%, the polyamide is 10–20%, and the water is 30–60% of the total weight of the composition. In each of these three aspects, in a preferred embodiment, the organic solvent includes hydrocarbon. In each of these three aspects, in a preferred embodiment, the organic solvent include an ester-containing compound. These compositions may contain optional components, some of which are described below.

In one aspect that provides a water-in-oil suspension of the present invention, the organic solvent is 1–99%, the polyamide is 1–40% and the water is 1–99% of the total weight is 10–60%, the polyamide is 5–30% and the water is 20–70% of the total weight of the composition. In another aspect, the organic solvent is 20–50%, the polyamide is 10–20%, and the water is 30–60% of the total weight of the composition. In each of these three aspects, in a preferred embodiment, the organic solvent includes hydrocarbon. In each of these three aspects, in a preferred embodiment, the organic solvent includes an ester-containing compound. These compositions may contain optional components, some of which are described below.

In one aspect that provides a water-in-oil emulsion of the present invention, the organic solvent is 1–99%, the polyamide is 1–40% and the water is 1–99% of the total weight is 10–60%, the polyamide is 5–30% and the water is 20–70% of the total weight of the composition. In another aspect, the organic solvent is 20–50%, the polyamide is 10–20%, and the water is 30–60% of the total weight of the composition. In each of these three aspects, in a preferred embodiment, the organic solvent includes hydrocarbon. In each of these three aspects, in a preferred embodiment, the organic solvent includes ester-containing compounds. These compositions may contain optional components, some of which are described below.

Optionally, the suspension of the invention may include a biocide, e.g., a bactericide. Exemplary bactericides include ACTICIDE® and KATHON® bactericides (Rohm & Haas, Philadelphia, Pa., U.S.A.; @rohmhaas.com); NIPACIDE® BIT 20 bactericide (Clariant, Mt. Holly, N.C., U.S.A.; @clariant.com); PROXEL® bactericide (Avecia Inc., Wilmington, Del., U.S.A.; @Pavecia.com); and TROYSAN 174® bactericide (Troy Corporation, Florham Park, N.J., U.S.A.; @troycorp.com), as well as analogous products from these and other manufacturers of bactericides. In general, the bactericide is incorporated into the suspension in an effective amount, which will normally be on the order of 0.1–5, preferably 0.1–2% by weight, based on the weight of the suspension.

Also optionally, the suspension of the invention may include a buffer to maintain a desired pH. Buffers for aqueous compositions are well known in the art, and may be used to buffer the suspensions of the present invention. In one embodiment, the buffering agent is an organic acid with a pKa within the range of 5.0–7.5 or a salt thereof, which can be used to buffer the suspension within the pH range of about 5.0–7.5. Inorganic acids may also be used as the buffering agent, where a pH of about 6–8 can be maintained using, for example, phosphate, acetate, bicarbonate or carbonate buffers. Buffering agents may be added to the suspensions of the invention at a concentration effective to achieve the buffering action, where this concentration will typically be within the range of 0.005 to 0.05 w/v %.

Optionally, the suspension of the invention may include a liquid in addition to water and organic solvent. For example, in one aspect, the suspension includes a silicone fluid. If the silicone fluid is miscible with the organic solvent, then the polyamide gels the silicon fluid at the same time that the organic solvent is gelled. If the silicone fluid is not compatible with the organic solvent or water, and is not gelled by the polyamide, then the silicon fluid will form droplets during preparation of a water-in-oil suspension, where those droplets will be held immobile by the elasticity of the gelled continuous phase. In this case, a tri-phasic suspension will be formed, having an aqueous discontinuous phase, a silicon oil discontinuous phase, and a continuous phase formed from polyamide and organic solvent. Exemplary silicone fluids are cyclomethicone, dimethicone and simethicone. Many silicon fluids are available commercially and may be used in the preparation of suspensions according to the present invention. For example, Aldrich (Milwaukee, Wis., U.S.A., @sigma-aldrich.com) sells poly(dimethylsiloxane) of various molecular weights. Silicone fluids are also available from Dow Corning Corporation (Midland, Mich., U.S.A.; @dowcorning.com) and General Electric Silicones (Waterford, N.Y., U.S.A.; @gesilicones.com).

In the general preparation of suspensions according to prior art techniques, it is common to include a surfactant among the components of the formulation. The surfactant assists in stabilizing the interface between the aqueous and non-aqueous phases. These same surfactants may optionally be included within the formulations to prepare suspensions according to the present invention, and exemplary surfactants are described below. However, in one aspect, the formulations of the present invention do not include a surfactant. In other aspects, the formulations of the present invention include less than 2.0, or 1.0, or 0.5 wt %, based on the total weight of the composition, of surfactant. Particularly when the polyamide gellant and the organic solvent form the continuous phase of a suspension of the present invention, it is typically unnecessary to include a surfactant in the composition because, as discussed below and surmised by the present inventors, the elastic property of the gelled organic phase is sufficient to stabilize the aqueous particles.

In general, surfactants useful in the present invention are a class of substances that are amphipathic (or amphiphilic) in nature (that is, possessing significant polar and nonpolar moieties on each molecule. Exemplary surfactants include, but are not limited to, soaps and detergents. In optional aspects, surfactants may be cationic, anionic, or zwitterionic (i.e., net neutral). In a preferred aspect, the surfactant is completely uncharged in structure (i.e., nonionic). Organic functional groups that may occur in surfactant molecular structure include, but are not limited to, ether and ester groups, often occurring in repeating polymeric units. When charged to a mixture of immiscible co-solvents (generally having the appearance of two separate well-defined phases), surfactant molecules form attractive interactions both with co-solvents of low polarity (such as organic solvents including hydrocarbons, via nonpolar attractive forces) and co-solvents of high polarity (such as water, via polar interactions such as hydrogen bonding). As a result of these interactions, surfactant molecules promote the co-dispersion of molecules of immiscible co-solvents, by disrupting the surface tension of at least one of the well-defined phases, thereby creating a greater surface area of interaction between the two phases. This action transforms the appearance of two separate phases into one of a single homogeneous mixture (that is, an emulsion) showing no well-defined segregation of substances.

Suitable surfactants that may be included within compositions of the present invention include, without limitation, nonionic alkyl phenol ethoxylate-containing compounds, e.g., TERGITOL™ NP-4 and TRIT available from Union Carbide); and SURFONIC™ N-40, SURFONIC™ DNP-100, and SURFONIC™ N-60 (all available from Huntsman Corporation, Salt Lake City, Utah); nonionic sorbitan ester-containing compounds, e.g., sorbitan monooleate (marketed as SPAN™ 80 by Uniqema, New Castle, Del.), and polyoxyethylene monolaurate (marketed as GLYCOSPERSE™ L20 by Lonza, Inc., Fair Lawn, N.J.). In one aspect the surfactant is known generally to be "skin-safe," i.e., safe for topical use on human skin, without causing adverse reactions such as allergies, rashes, and hives. Examples of skin-safe surfactants include, but are not limited to, sorbitan monooleate and sodium lauryl sulfate (an anionic surfactant).

When the suspension of the present invention is a dispersion of polyamide and gelled organic solvent in an aqueous continuous phase, the dispersion preferably contains one or more surfactants in an amount sufficient to stabilize the particles of polyamide in the continuous phase.

A surprising aspect of the present invention is a composition for an emulsion, preferably a water-in-oil emulsion, which is stable without the need for added surfactant.

Without wishing to be bound by the following explanation, it is surmised by he present inventors that the polyamide is able to gel the organic solvent. In a preferred aspect of the invention, the polyamide and organic solvent are selected and combined in a quantity such that the polyamide is able to gel the solvent. The water then disperses throughout the gel and is essentially immobile due to the high elasticity of the organic gel. Thus, in the presence of dimer acid-based polyamides, preferably ester-terminated polyamides (ETPA) or tertiary amide-terminated polyamides (ATPA), oil and water may be maintained in an emulsion form without the need for surfactants to stabilize the emulsion form.

In one aspect, the present invention provides a composition comprising a dispersed aqueous phase, a continuous organic phase, and a polymerized fatty acid-based polyamide, wherein the continuous phase comprises an organic solvent that is immiscible with water. In a further aspect of this composition, the dispersed aqueous phase and continuous organic phase form an emulsion. A preferred aspect is one wherein the composition is indicative of a water-in-oil emulsion, in that the emulsion may be placed on top of water and maintains a separate structure, i.e., the emulsion does not dissolve into the water. In another preferred aspect, dispersion of the dispersed phase through the continuous phase is of an even distribution, generating a homogenous-appearing emulsion.

Each emulsion type has its advantages. The oil-in-water-emulsion is non-occlusive, non-greasy, removed easily from skin, aesthetically pleasing, and economical, thus is the preferred emulsion type for many topical cosmetic applications (skin creams, etc.). Water-in-oil emulsions, while greasier in feel and more prone to streaking when used in cosmetics, exhibit greater water repellency, thus may be preferred in products such as (without limitation) polishes, lotions for "extra-dry" skin, and waterproof sunscreens. Biologically active agents, preferably water-soluble biologically active agents, may be included in the emulsion and thereby be delivered to, e.g., the skin by topical application of the emulsion. In one aspect of the invention, the suspension has the consistency and appearance of a white or translucent cream, where the suspension can have varying degrees of stiffness. A further aspect of the suspension of the invention is a formulation as a cosmetic product further comprising fragrance.

As mentioned above, in one aspect of the emulsion of the invention, the composition of the emulsion comprises a surfactant. Preferred aspects of surfactants used in this invention are described hereinbefore. In a preferred emulsion composition comprising surfactant, dispersion of the dispersed phase through the continuous phase is of an even distribution, generating a homogenous emulsion. In other aspects of the emulsion composition comprising surfactant, the emulsion has the consistency and appearance of a white or translucent cream; and this emulsion can have varying degrees of stiffness. A further aspect of the emulsion of the invention is a formulation as a cosmetic product further comprising fragrance.

Another aspect of the present invention is methodology useful to prepare a suspension of this invention. When the suspension is a water-in-oil emulsion, the emulsion may be prepared as follows: organic solvent, polyamide, and surfactant (if used) are charged to a reaction flask and heated to about 90–120° C. with agitation until the components are dispersed evenly to form a mixture. Water is then added drop-wise with stirring while maintaining the temperature of the mixture at about 75–80° C. until the water is incorporated fully into the mixture.

Upon cooling to about 60° C., the water-in-oil emulsion is transferred to a storage container and allowed to cool to room temperature.

In another aspect of the method, 0.1–10% of the water (by weight, based on the total weight of the water that is desirably present in the final product) is incorporated along with the organic solvent, before the remaining water is added drop-wise to the mixture as indicated above. In another aspect of the method, the initial mixture (containing organic solvent, polyamide, and optionally surfactant) is cooled to about 50–60° C. before additional organic solvent and water are incorporated into the mixture using a blender. In a separate aspect of the method, the entire quantity of water is added to the reaction vessel concurrently with the organic solvent, and the entire composition is mixed, heated with stirring, and cooled to form the emulsion. In another aspect of the method, the mixture is kept under an atmosphere of nitrogen gas during the heating process.

The mixture of water, organic solvent and polyamide is preferably stirred while in a molten form so as to achieve a homogeneous distribution of the water in the organic phase. The emulsions of the present invention can be formed without special high speed dispersing equipment, although use of such equipment allows formation of stable emulsions at reduced temperatures.

This method of the present invention results in the formation of a stiff uniform cream that feels oily and does not dissipate when additional water is added (thus, a water-in-oil emulsion). Stiffness of the cream ranges from soft and greasy, to a formulation that possesses enough stiffness to support not only its own weight by a small amount of external pressure. Softer creams may find use as bases for such products as, without limitation, cosmetics, insect repellents, sunscreens, shoe polish, furniture polish, and topical medications. Stiffer creams may find use as bases for such products as, without limitation, facial masks, car and metal polish, and lubricants. It should be mentioned, however, that if any active ingredients in these products are heat-sensitive, care should be taken not to subject such agents to procedural steps requiring detrimental heat.

An oil-in-water suspension may be prepared using a polyamide gellant, water and a surfactant. If the dispersed phase should be gelled organic solvent, then it will be necessary to include organic solvent in the formulation. Procedures to make polyamide dispersions are known in the art. See, e.g., U.S. Pat. Nos. 5,095,058; 5,428,083; 5,539,025; 5,723,538; 5,747,555; 5,770,680; 5,804,682; 5,948,880; and 6,077,900.

Regardless of whether the suspension contains a surfactant, the suspension of the present invention is useful to impart sheen or a polished appearance to metal, e.g., the suspension is useful as a polishing agent for a solid substrate, e.g., a car. Thus, in various aspects, the present invention provides a composition useful as a polish or wax, and methods of imparting sheen to a substrate, such as a metallic substrate, using the suspensions of the present invention. For example, in a suspension that does not include a surfactant, the present invention provides a suspension useful as a polish that contains polymerized fatty acid-based polyamide gellant, e.g., ETPA or ATPA. In various preferred embodiments, the suspension contains, in addition to other optional ingredients, 30–80%, or 30–70%, or 30–65%, or 30–60%, or 35–80%, or 35–70%, or 35–65%, or 35–60%, or 40–80%, or 40–70%, or 40–65%, or 40–60%, or 45–80%, or 45–70%, or 45–65%, or 45–60% water; the suspension contains 1–10%, or 1–8%, or 1–6%, or 2–10%, or 2–8%, or 2–6%, or 3–10%, or 3–8%, or 3–6% polymerized fatty acid-based polyamide, e.g., ETPA or ATPA; the suspension contains 0%, or 15–40%, or 15–35%, or 15–30%, or 15–25%, or 20–40%, or 20–35%, or 20–30%, or 20–25%, or 25–40%, or 25–35%, or 25–30%, or 30–40%, or 30–35% mineral oil or mixture of mineral oils; the suspension contains 0%, or 0.5–10%, or 1–10%, or 1.5–10%, or 2–10%, or 3–10%, or 0.5–8%, or 1–8%, or 1.5–8%, or 2–8%, or 3–8%, or 0.5–6%, or 1–6%, or 1.5–6%, or 2–6%, or 3–6%, or 0.5–5%, or 1–5%, or 1.5–5%, 2–5%, or 3–5%, or 0.5–4%, or 1–4%, or 1.5–4% wax, such as paraffin wax and/or microcrystalline wax; the suspension contains 0%, or 1–20%, or 5–20%, or 7–20%, or 8–20%, or 9–20%, or 10–20%, or 1–15%, or 5–15%, or 7–15%, or 8–15%, or 9–15%, or 1–12%, or 5–12%, or 7–12% of diester having a melting point above room temperature, e.g., solid diester of the formula $C_{2\text{-}14}$—O(C=O—$C_{2\text{-}8}$—C(=O)O—$C_{2\text{-}14}$ where $C_{2\text{-}14}$ represents a hydrocarbon group having at least 2 and up to as many as 14 carbons; the suspension contains 0%, or 0.5–8%, or 1–8%, or 2–8%, or 3–8%, or 4–8%, or 0.5–6%, or 1–6%, or 2–6%, or 3–6%, or 4–6% volatile liquid having a melting point below room temperature and a boiling point below 100° C., e.g., hexane or mineral spirits, where each of the percentage values and ranges disclosed herein are in weight percent based on the total weight of the suspension.

In a preferred embodiment, for example when the suspension is intended for use as a car polish, the suspension contains wax. Suitable waxes that may be included in the composition include fully refined paraffin wax, or a partially refined (e.g., scale or slack) paraffin wax. The wax may be petroleum wax, including one or more of a paraffin, ceresine, ozokerite and microcrystalline wax. The wax may be a natural wax, such as candelilla wax, beeswax, or carnauba wax. The wax may be a synthetic wax, such as a product of the Fischer-Tropsch process, or a polyethylene wax. Waxes spanning a range of melt points are commercially available and are suitable for incorporation into a formulation according to the present invention. For example Moore & Munger, Inc. (Shelton, Conn., U.S.A.; @mooremunger.com) sells paraffin waxes with melt points (as measured by ASTM D87, ° F.) of 126, 131, 136, 141, 142, 151, 156, 157 and 159. The wax may be a microcrystalline wax, where Moore & Munger, Inc. sells microcrystalline waxes with melt points (ASMT D87, ° F.) of 130, 156, 161, 165, 170, 175, 176, 178, 179, 181, 186, 188, 195 and 196. The wax may be a synthetic wax produced by the Fischer-Tropsch process. Moore & Munger, Inc. sells synthetic waxes having softening points (Ring & Ball, ° F.) ranging from 203–212. Other vendors of suitable waxes include, for example, Hase Petroleum Wax Company (Arlington Heights, Ill., U.S.A.; @hpwax.com), and the International Group, Inc. (Wayne, Pa., U.S.A.; @igwax.com).

The wax may be in solid form when it is added to the suspension-forming composition, or the wax may be in liquid form, e.g., molten wax or dissolved wax or an emulsion form of the wax. In one aspect, the wax is incorporated into the composition via an aqueous wax emulsion. Aqueous wax emulsions are available from many commercial sources, e.g., MICROLUBE® and PARA-COL® wax emulsions are available from Hercules Incorporated (Wilmington, Del., U.S.A.; @herc.com); and BASOPHOB® wax emulsions are available from BASF Corporation (Mt. Olive, N.J., U.S.A.; @basf.de).

In another preferred embodiment, the suspension contains liquid hydrocarbon, e.g., mineral oil and/or mineral spirits, optionally in addition to the wax. Other suitable liquid hydrocarbons include $C_6$-$C_{10}$ hydrocarbons. Petroleum ether is another suitable liquid hydrocarbon. In another preferred embodiment, the suspension contains a solid diester, e.g., a solid diester of the formula $C_{2\text{-}14}$—O (C=O)—$C_{2\text{-}8}$—C(=O)O—$C_{2\text{-}14}$, optionally in addition to the liquid hydrocarbon and/or optionally in addition to the wax. In one embodiment, the suspension suitable for use as a polish contains 30–80% water, 1–10% ETPA or ATPA, 0.5–10% wax, 15–40% mineral oil, and 0.5–8% volatile hydrocarbon. Optionally, the suspension may additionally contain 1–20% diester. Optionally, the suspension does not contain surfactant. Optionally, the suspension does contain surfactant. Optionally, the suspension contains surfactant in an amount of 0.5–8%, or 1–8%, or 2–8%, or 3–8%, or 4–8%, or 0.5–6%, or 1–6%, or 2–6%, or 3–6%, or 4–6%, or 0.5–5%, or 1.5–5%, or or 2–5%, where the surfactant is preferably non-ionic.

Suspensions suitable for use as car polishes that incorporate wax may be prepared by combining all of the non-aqueous ingredients into a reaction vessel, melting the non-aqueous ingredients and stirring to achieve a homogeneous mixture, heating the homogeneous mixture to about or slightly above 100° C., and then adding water to the mixture in a drop-wise fashion with stirring. Upon cooling, a suspension with a creamy consistency will typically be produced. This suspension may be rubbed onto or otherwise applied to a metallic or other substrate, to form a film on the substrate. After a brief time, the film may be rubbed off from the substrate using a cloth, leaving a polished substrate. While metal is a preferred substrate, other solid substrates that may be polished according to the present invention include wood and plastic.

In the following examples, all chemicals were of reagent grade unless noted otherwise, and were obtained from commercial supply houses such as Aldrich Chemical Co. (Milwaukee, Wis.). DRAKEOL 7™ mineral oil was obtained from Penreco (Houston, Tex.). MAGIESOL M-47™ white mineral oil is available from many suppliers, and has a flashpoint of 107° C., paraffinic carbon atom % of 62.2%, naphthenic carbon atom % of 37.0%, aromatic carbon atom % of 0.8%, average molecular weight of 203 g/mol, boiling point of 239–277° C.; UNICLEAR 100™, SYLVAGEL 5000™ and SYLVAGEL 6000™ are each polymerized fatty acid-based polyamides (and more specifically ETPAs) while SYLVACLEAR A-200™ is an ATPA, each being obtained from Arizona Chemical (Jacksonville, Fla.). Dicapryl adipate, marketed as ARIZONA SP 100™, was also obtained from Arizona Chemical. SYLVALITE RE105™ is a rosin ester obtained from Arizona Chemical (Jacksonville, Fla., U.S.A.). TERGITOL NP-4 ™ nonylphenol ethoxylate surfactant was obtained from Union Carbide. SURFONIC 40™ nonylphenol ethoxylate surfactant was obtained from Huntsman Corporation (Salt Lake City, Utah). The surfactant sucrose distearate, marketed under the name CRODESTA F-10™, was obtained from Croda Inc. (Parsippany, N.J.). SPAN 80™ sorbitan monooleate surfactant was obtained from Uniqema (New Castle, Del.). SURFONIC L24-3™ is a surfactant produced by Huntsman Chemical (Salt Lake City, Utah, U.S.A.), prepared from C12–C16 synthetic alcohols and 3 moles of ethylene oxide, having a CAS Registry No. of 68551-12-2. ISOPAR™ H petroleum ether was obtained from Exxon (Fairfax, Va.). EMPOL™ 1008 polymerized fatty acid is a dimer acid, obtained from Henkel Corporation (Ambler, Pa.). VM & P mineral spirits may be obtained from many sources, including Parks Corporation (Fall River, Mass., U.S.A.) and has Chemical Abstract Service (CAS) Registry No. 8032-32-4; Stearyl alcohol, marketed as ALFOL™America Inc.

(Houston, Tex.). PARAFLINT™ hydrocarbon-based microcrystalline waxes are available from several suppliers and come in various grades, where PARAFLINT H4™ has a softening point of 110.3° C.

EXAMPLES

Example 1

Water-In-Oil Emulsion Using ETPA and Tergitol™ NP-4 Surfactant

This example shows that a smooth aqueous cream can be made from ETPA in the presence of TERGITOL™ NP-4 surfactant.

A reaction vessel was charged with (by percentage of final mixture weight) 48.31% DRAKEOL™ 7 mineral oil, 2.90% TERGITOL™ NP-4 surfactant, 0.24% water, and 12.32% UNICLEAR™ 100 ester-terminated polyamide, heated to 100° C. with stirring, until molten and homogeneous, then cooled. Subsequently, the reaction vessel was charged with additional water (36.23%, to a final mixture weight of 41.4 grams) with reheating and continued stirring, followed by cooling of the reaction mixture to room temperature, resulting in a smooth cream indicative of a water-in-oil emulsion.

Example 2

Water-In-Oil Emulsion Using ETPA and SPAN™ 80 Surfactant

This example shows that a smooth aqueous cream can be made from ETPA in the presence of SPAN™ 80 surfactant.

A reaction vessel was charged with (by percentage of final mixture weight) 23.03% DRAKEOL™ 7 mineral oil, 11.52% UNICLEAR™ 100 ester-terminated polyamide, and 4.03% SPAN™ 80 surfactant. This mixture was heated to 110° C. with stirring until molten and homogeneous, and then cooled to about 80° C. Subsequent addition of water (61.42%, to a final mixture weight of 52.1 grams) with continued stirring, followed by cooling of the reaction mixture to room temperature, resulted in a smooth cream indicative of a water-in-oil emulsion.

Example 3

Formation of Water-In-Oil Emulsion with ETPA and Tergitol™ NP-4 Surfactant

This example shows that two immiscible phases can coalesce into an ETPA-containing homogeneous emulsion with increasing surfactant.

Initially, a reaction vessel was charged with DRAKEOL™ 7 mineral oil, UNICLEAR™ 100 ester-terminated polyamide, and TERGITOL™ NP-4 surfactant in the initial proportions indicated in Table 1, and heated to 110° C. with stirring until molten and homogeneous. Addition of water (as indicated, to a total mixture weight of 39.99 grams) with continued stirring converted the reaction mixture into two clearly defined phases: a water-like bottom phase and a cake-like top phase. The reaction vessel was then charged with 0.6 grams additional TERGITOL™ NP-4 surfactant (to the intermediate mixture percentages indicated in Table 1) with reheating and stirring, followed by cooling to room temperature, yielding a lumpy emulsion with exclusion of some water. Finally, the reaction vessel was charged with 0.6 grams additional TERGITOL™ NP-4 surfactant (to the final mixture percentages indicated in Table 1) with reheating and stirring, followed by cooling to room temperature, yielding a smooth homogeneous creamy emulsion.

TABLE 1

COMPONENT PERCENTAGES USED TO FORM A WATER-IN-OIL EMULSION

| Component | Weight % (Initial) | Weight % (Intermediate) | Weight % (Final) |
| --- | --- | --- | --- |
| DRAKEOL™ 7 | 19.45 | 19.17 | 18.89 |
| UNICLEAR™ 100 | 9.73 | 9.58 | 9.44 |
| TERGITOL™ NP-4 | 0.08 | 2.27 | 3.69 |
| Water | 70.02 | 68.98 | 67.98 |
| Appearance: | Two-phase mixture | Lumpy emulsion, with some water exclusion | Homogeneous emulsion |

Example 4

Water-In-Oil Emulsion Using ETPA and Tergitol™ NP-4 Surfactant

This example shows the formation of a smooth cream using the same components (albeit in different amounts) of Example 1, but with all components charged to the reaction flask prior to heating.

A reaction vessel was charged with (by weight) 53.01% water, 28.92% DRAKEOL™ 7 mineral oil, 14.46% UNICLEAR™ 100 ester-terminated polyamide, and 3.61% TERGITOL™ NP-4 surfactant (to a final mixture weight of 41.5 grams). The mixture was heated to about 100° C. with stirring until molten and homogeneous, then cooled to room temperature, resulting in a smooth homogeneous cream indicative of a water-in-oil emulsion. The cream product was stiff enough to hold its shape and support weight.

Example 5

Water-In-Oil Emulsion Using ETPA with Various Surfactants

This example demonstrates that various surfactants can be used to create ETPA-containing water-in-oil emulsions.

A reaction vessel was charged with (by weight) 53.01% water, 28.92% DRAKEOL™ 7 mineral oil, 14.46% UNICLEAR™ 100 ester-terminated polyamide, and 3.61% surfactant (indicated in Table 2), and heated to about 100° C. with stirring until the contents were molten and homogeneous. Cooling of the reaction mixtures to room temperature resulted in creams indicative of water-in-oil emulsions, with varying degrees of stiffness and water exclusion (as indicated in Table 2).

TABLE 2

SURFACTANTS USED TO FORM A WATER-IN-OIL EMULSION

| Surfactant | Appearance of Final Mixture | Exclusion of Water (% of the mixture weight) |
| --- | --- | --- |
| SURFONIC™ 40 | Greasy cream | 16.14 |
| CRODESTA™ F-10 | Smooth stiff white cream | None |

Example 6

Water-In-Oil Emulsion Using ETPA with Petroleum Ether

In this example, ISOPAR™ H petroleum ether was used as the organic phase in the formation of the emulsion.

A reaction flask was charged with (by weight) 53.44% water, 3.20% CRODESTA™ F-10 surfactant, 14.48% UNICLEAR™ 100 ester-terminated polyamide, and 28.89% ISOPAR™ H petroleum ether. This mixture was then heated to about 100° C. with stirring to produce a milky suspension. Subsequent cooling yielded a homogeneous cream that was stiff, smooth, and water-repellent in nature.

Example 7

Water-In-Oil Emulsion Using ETPA with Ester

This example provides a water-in-oil emulsion formed with the use of an ester as the organic phase.

A reaction vessel was charged with (by percentage of final mixture weight) 28.36% isopropyl isomyristate, 13.11% UNICLEAR™ 100 ester-terminated polyamide, and 3.67% SPAN™ 80 surfactant, heated to about 100° C. with stirring until molten and homogeneous, then cooled. The reaction mixture was then reheated, charged drop-wise with water (45.14%, to a final mixture weight of 43.02 grams), and cooled. The resulting product was a stiff homogeneous emulsion (i.e., does not flow when strongly shaken) that excluded water (excluded amount: about 10.5% of the total weight of the mixture).

Example 8

Water-In-Oil Emulsion Using ATPA with Ester

This example shows a water-in-oil emulsion formed with the use of ATPA.

A reaction flask was charged with (by percentage of final mixture weight) 29.17% isopropyl isomyristate, 14.11% SYLVACLEAR A-200 tertiary amide-terminated polyamide, and 3.66% TERGITOL™ NP-4 surfactant. The flask contents were heated to about 100° C. with stirring until molten and homogeneous, then cooled to about 87° C. The reaction flask was then charged drop-wise with water (53.06%, to a final mixture weight of 41.83 grams), and further cooled to about 80° C. The resulting product was a stiff water-in-oil emulsion that excluded water (excluded amount: 12.91% of the total weight of the mixture), and had a slight grainy appearance.

Example 9

Formation of ETPA for Water-In-Oil Emulsion

This example demonstrates a typical procedure for creating ETPA to be used in the formulation of water-in-oil emulsions in the subsequent example.

Using the amounts shown in Table 3, EMPOL™ 1008 polymerized fatty acid and stearyl alcohol were combined and heated to about 130° C. Ethylene diamine was added and heating was continued to about 200° C. The mixture was maintained at about 200° C. until the acid number of the mixture was less than 17. The reaction mixture was cooled to about 150° C. and discharged from the reactor. About 100 grams of polyamide was prepared by this process.

It should be noted that in Table 3 the term "equivalent(s)" is intended to have its standard meaning as used in the art. Briefly, the term "equivalent(s)" refers to the number of reactive groups present in a molar quantity of a molecule. In this example, one mole of stearyl alcohol has one equivalent of alcohol, while one mole of ethylene diamine has two equivalents of amine.

TABLE 3

COMPONENT PERCENTAGES USED TO FORM ETPA FOR WATER-IN-OIL EMULSION

| Component | % Equivalents | Weight % |
| --- | --- | --- |
| EMPOL ™ 1008 | 100 | 74.1 |
| Stearyl alcohol | 30 | 20.8 |
| Ethylene diamine | 69 | 5.0 |

Example 10

Water-In-Oil Emulsion Using ETPA Without Surfactant

Two reaction flasks were charged with mineral oil, dicapryl adipate, and ETPA (as prepared in Example 9) in the proportions indicated in Table 4. This reaction mixture was heated to about 100° C. with stirring until molten and homogeneous. Water was then added drop-wise to the final mixture weights indicated in Table 4, and the resulting mixtures were cooled. Each formulation resulted in a homogeneous emulsion having the consistency of a stiff smooth cream.

TABLE 4

COMPONENT PERCENTAGES USED TO FORM SURFACTANT-FREE WATER-IN-OIL EMULSION

| Component | Weight %, Mixture 1 | Weight %, Mixture 2 |
| --- | --- | --- |
| DRAKEOL ™ 7 mineral oil | 30.51 | 22.50 |
| Dicapryl adipate | 10.17 | 7.50 |
| ETPA | 10.17 | 7.50 |
| Water | 49.15 | 62.50 |
| Total Mixture Weight | 59.0 grams | 80.0 grams |

Example 11

Water-In-Oil Emulsion Using ETPA Without Surfactant, at Reduced Temperature

This example shows the formation of a stable water-in-oil emulsion in the absence of surfactant, using a reduced temperature with increased agitation. A reaction vessel was charged with (by percentage of final mixture weight) 5.42% DRAKEOL™ 7 mineral oil, 11.28% UNICLEAR™ 100 ester-terminated polyamide, 22.56% dicapryl adipate, 1.35% 1-octyldodecanol, and 0.27% floral fragrance oil. This mixture was heated to 110° C. with stirring until molten and homogeneous, then cooled to about 60° C. The reaction flask was then charged with 4.20% cyclomethicone and 54.92% water (to a final mixture weight of 101.15 grams), and at about 50° C. was dispersed with high shear (using a blender) for about 10 minutes at a moderate motor speed. Upon cooling to room temperature, the resulting product was a white homogeneous cream that was smooth and stiff (i.e., does not flow when strongly shaken).

Example 12

A reaction vessel, equipped with a magnetic stir bar, was charged with (by percentage of final weight mixture) 30.5% DRAKEOL™ 7 mineral oil, 10.2% Arizona SP-100™ dicapryl adipate, 4% SYLVAGEL 6000™ ester-terminated polyamide resin, 2% PARAFLINT™ H4 microcrystalline wax, 2% MAGIESOL™ M-47 white mineral oil and 2% VM&P mineral spirits and the mixture was heated to above 100° C. with stirring to form a homogeneous mixture. Subsequently, the reaction vessel was charged drop-wise with 49.3% water, heated to above 100° C. with stirring to form a homogeneous mixture, followed by cooling to room temperature with stirring, resulting in a white, homogeneous surfactant-free soft cream indicative of a water-in-oil emulsion.

Example 13

A reaction vessel, equipped with a magnetic stir bar, was charged with (by percentage of final weight mixture) 22.5% DRAKEOL 7™ mineral oil, 7.5% Arizona SP-100™ ester, 3% SYLVAGEL 6000™ ester-terminated polyamide resin, 1.5% PARAFLINT H4™ microcrystalline wax, 1.5% Magiesol M-47™ white mineral oil and 1.5% VM & P mineral spirits and the mixture was heated to above 100° C. with stirring to form a homogeneous mixture. Subsequently, the reaction vessel was charged drop-wise with 62.5% water, heated to above 100° C. with stirring to form a homogeneous mixture, followed by cooling to room temperature with stirring, resulting in a white, homogeneous surfactant-free soft cream indicative of a water-in-oil emulsion.

Example 14

A reaction vessel, equipped with a magnetic stir bar, was charged with (by percentage of final weight mixture) 20% DRAKEOL 7™ mineral oil, 10% Arizona SP-100™ ester, 4% SYLVAGEL 6000™ ester-terminated polyamide resin, 2% PARAFLINT H4™ microcrystalline wax, 2% MAGIESOL M-47™ white mineral oil and 2% VM & P mineral spirits and the mixture was heated to above 100° C. with stirring to form a homogeneous mixture. Subsequently, the reaction vessel was charged drop-wise with 60% water, heated to above 100° C. with stirring to form a homogeneous mixture, followed by cooling to room temperature with stirring, resulting in a white, homogeneous surfactant-free soft cream indicative of a water-in-oil emulsion.

Example 15

This example shows that a white, aqueous-based soft cream cannot be made from ETPA in the absence of a surfactant if the level of DRAKEOL 7™ mineral oil is not sufficient to form a water-in-oil emulsion. A reaction vessel, equipped with a magnetic stir bar, was charged with (by percentage of final weight mixture) 10% DRAKEOL 7™ mineral oil, 10% Arizona SP-100™ ester, 8% SYLVAGEL 6000™ ester-terminated polyamide resin, 4% PARAFLINT H4™ microcrystalline wax, 4% MAGIESOL M-47™ white mineral oil and 4% VM & P mineral spirits and the mixture was heated to above 100° C. with stirring to form a homogeneous mixture. Subsequently, the reaction vessel was charged drop-wise with 60% water, heated to above 100° C. with stirring to form a homogeneous, cloudy mixture, followed by cooling to room temperature with stirring, resulting in a two separate layers. The top layer comprised a white, creamy solid while the bottom layer was a clear liquid.

Example 16

A reaction vessel, equipped with a magnetic stir bar, was charged with (by percentage of final weight mixture) 30% DRAKEOL 7™ mineral oil, 10% Arizona SP-100™ ester, 8% SYLVAGEL 6000™ ester-terminated polyamide resin, 4% PARAFLINT H4™ microcrystalline wax, 4% MAGIESOL M-47™ white mineral oil and 4% VM & P mineral spirits and the mixture was heated to above 100° C. with stirring to form a homogeneous mixture. Subsequently, the reaction vessel was charged drop-wise with 40% water, heated to above 100° C. with stirring to form a homogeneous mixture, followed by cooling to room temperature with stirring, resulting in a white, homogeneous soft cream indicative of a water-in-oil emulsion.

Example 17

This example shows that a white, aqueous-based soft cream can be made from ETPA in the absence of a surfactant. A reaction vessel, equipped with a magnetic stir bar, was charged with (by percentage of final weight mixture) 20% DRAKEOL 7™ mineral oil, 10% Arizona SP-100™ ester, 8% SYLVAGEL 6000™ ester-terminated polyamide resin, 4% PARAFLINT H4™ microcrystalline wax, 4% MAGIESOL M-47™ white mineral oil and 4% VM & P mineral spirits and the mixture was heated to above 100° C. with stirring to form a homogeneous mixture. Subsequently, the reaction vessel was charged drop-wise with 50% water, heated to above 100° C. with stirring to form a white, homogeneous mixture, followed by cooling to room temperature with stirring, resulting in a white, homogeneous soft cream indicative of a water-in-oil emulsion.

Example 18

This example shows that a white, flocculative aqueous-based cream can be made from ETPA in the presence of a surfactant.

A reaction vessel, equipped with a magnetic stir bar, was charged with (by percentage of final weight mixture) 48.30% DRAKEOL 7™ mineral oil, 2.90% SURFONIC L24-3™ surfactant, 0.24% water and 12.32% PC0063-4 (contains 40% SYLVAGEL 6000™ ester-terminated polyamide resin, 20% PARAFLINT H4™ microcrystalline wax, 20% MAGIESOL M-47™ white mineral oil and 20% VM & P mineral spirits), heated to above 100° C. with stirring to form a homogeneous mixture. Subsequently, the reaction vessel was charged with additional water (36.24%) with heating and stirring, followed by cooling to room temperature with stirring, resulting in a white, flocculative cream indicative of a water-in-oil emulsion.

Example 19

A reaction vessel, equipped with a magnetic stir bar, was charged with (by percentage of final weight mixture) 23.03% DRAKEOL 7 mineral oil™, 4.0% SURFONIC L24-3™ surfactant and 11.52% PC0063-4 (contains 40% SYLVAGEL 6000™ ester-terminated polyamide resin, 20% PARAFLINT H4™ microcrystalline wax, 20% MAGIESOL M-47™ white mineral oil and 20% VM & P mineral spirits), heated to above 100° C. with stirring to form a homogeneous mixture. Subsequently, the reaction vessel was charged with additional water (61.42%) with heating and stirring, followed by cooling to room temperature with stirring, resulting in a white, viscous (thickened) liquid with a cream-like texture indicative of a water-in-oil emulsion.

Example 20

A reaction vessel, equipped with a magnetic stir bar, was charged with (by percentage of final weight mixture) 18.89% DRAKEOL 7™ mineral oil, 3.7% SURFONIC L24-3™ surfactant, 9.4% PC0063-4 (contains 40% SYLVAGEL 6000™ ester-terminated polyamide resin, 20%

PARAFLINT H4™ microcrystalline wax, 20% MAGIESOL M-47™ white mineral oil and 20% VM & P mineral spirits) and 68.0% water, heated to above 100° C. with stirring to form a homogeneous mixture, followed by cooling to room temperature with stirring, resulting in a white, viscous (thickened) liquid with a cream-like texture indicative of a water-in-oil emulsion.

Example 21

A reaction vessel, equipped with a magnetic stir bar, was charged with (by percentage of final weight mixture) 29.85% DRAKEOL 7™ mineral oil, 2.99% SURFONIC L24-3™ surfactant, 36.97% water and 30.19% PC0063-4 (contains 40% SYLVAGEL 6000™ ester-terminated polyamide resin, 20% PARAFLINT H4™ microcrystalline wax, 20% MAGIESOL M-47™ white mineral oil and 20% VM & P mineral spirits), heated to above 100° C. with stirring to form a homogeneous mixture, followed by cooling to room temperature with stirring, resulting in a white cream, with a soft paste texture, indicative of a water-in-oil emulsion.

Example 22

A reaction vessel, equipped with a magnetic stir bar, was charged with (by percentage of final weight mixture) 29.94% DRAKEOL 7™ mineral oil, 3.02% SURFONIC L24-3™ surfactant, 36.97% water and 30.06% PC0063-3 (contains 40% SYLVAGEL 6000™ ester-terminated polyamide resin, 15% PARAFLINT H4™ microcrystalline wax, 20% MAGIESOL M-47™ white mineral oil, 20% VM & P mineral spirits and 5% SYLVALITE RE105™ rosin ester), heated to above 100° C. with stirring to form a homogeneous mixture, followed by cooling to room temperature with stirring, resulting in a white cream, with a soft paste texture, indicative of a water-in-oil emulsion.

Example 23

A reaction vessel, equipped with a magnetic stir bar, was charged with (by percentage of final weight mixture) 20% SYLVAGEL 6000™ ester-terminated polyamide resin, 10% PARAFLINT H4™ microcrystalline wax, 10% MAGIESOL M-47™ white mineral oil and 10% VM & P mineral spirits and the mixture was heated to above 100° C. with stirring to form a homogeneous mixture. Then 7% DRAKEOL 7™ mineral oil and 3% SURFONIC L24-3™ surfactant were charged to the reaction vessel and heated to above 100° C. with stirring to form a homogeneous mixture. Subsequently, the reaction vessel was charged with 40% water, heated to above 100° C. with stirring to form a homogeneous mixture, followed by cooling to room temperature with stirring, resulting in a white cream, with a soft paste texture, indicative of a water-in-oil emulsion.

Example 24

A reaction vessel, equipped with a magnetic stir bar, was charged with (by percentage of final weight mixture) 20% SYLVAGEL 6000™ ester-terminated polyamide resin, 10% PARAFLINT H4™ microcrystalline wax, 10% MAGIESOL M-47™ white mineral oil, 10% VM & P mineral spirits and 10% DRAKEOL 7™ mineral oil and the mixture was heated to above 100° C. with stirring to form a homogeneous mixture. Subsequently, the reaction vessel was charged with 40% water, heated to above 100° C. with stirring to form a homogeneous mixture, followed by cooling to room temperature with stirring, resulting in two separate layers. A white cream, with a soft paste texture, was observed on top while a clear liquid remained in the bottom layer.

Example 25

A reaction vessel, equipped with a magnetic stir bar, was charged with (by percentage of final weight mixture) 20% SYLVAGEL 6000™ ester-terminated polyamide resin, 10% PARAFLINT H4™ microcrystalline wax, 10% MAGIESOL M-47™ white mineral oil and 10% VM & P mineral spirits and the mixture was heated to above 100° C. with stirring to form a homogeneous mixture. Then 3% SURFONIC L24-3™ surfactant and 47% water were charged to the reaction vessel and heated to above 100° C. with stirring to form a homogeneous mixture, followed by cooling to room temperature with stirring, resulting in a white viscous (thickened) liquid, with a flocculative texture, was observed at room temperature. When shaken, the mixture provided a more homogeneous liquid. After 24 hours of setting at room temperature, two separate layers had developed. The top layer was comprised of a creamy, white solid while the lower layer was a cloudy liquid.

Example 26

This example shows that a white, aqueous-based cream (soft paste) can be made from ETPA in the presence of a surfactant. A reaction vessel, equipped with a magnetic stir bar, was charged with (by percentage of final weight mixture) 30% SYLVAGEL 6000™ ester-terminated polyamide resin, 10% PARAFLINT H4™ microcrystalline wax, 10% MAGIESOL M-47™ white mineral oil and 10% VM & P mineral spirits and the mixture was heated to above 100° C. with stirring to form a homogeneous mixture. Then 7% DRAKEOL 7™ mineral oil and 3% SURFONIC L24-3™ surfactant were charged to the reaction vessel and heated to above 100° C. with stirring to form a homogeneous mixture. Subsequently, the reaction vessel was charged with 30% water, heated to above 100° C. with stirring to form a homogeneous mixture, followed by cooling to room temperature with stirring, resulting in a white cream, with a soft paste texture, indicative of a water-in-oil emulsion.

Example 27

A reaction vessel, equipped with a magnetic stir bar, was charged with (by percentage of final weight mixture) 20% SYLVAGEL 6000™ ester-terminated polyamide resin, 10% PARAFLINT H4™ microcrystalline wax, 10% MAGIESOL M-47™ white mineral oil and 10% VM & P mineral spirits and the mixture was heated to above 100° C. with stirring to form a homogeneous mixture. Then 10% DRAKEOL 7™ mineral oil and 5% SURFONIC L24-3™ surfactant were charged to the reaction vessel and heated to above 100° C. with stirring to form a homogeneous mixture. Subsequently, the reaction vessel was charged with 35% water, heated to above 100° C. with stirring to form a homogeneous mixture, followed by cooling to room temperature with stirring, resulting in a white cream, with a soft paste texture, indicative of a water-in-oil emulsion.

Example 28

A reaction vessel, equipped with a magnetic stir bar, was charged with (by percentage of final weight mixture) 20% SYLVACLEAR A-200™ ester-terminated polyamide resin, 10% PARAFLINT H4™ microcrystalline wax, 10% MAGIESOL M-47™ white mineral oil and 10% VM & P mineral spirits and the mixture heated to above 100° C. with stirring to form a homogeneous mixture. Then 7% DRAKEOL 7™ mineral oil and 3% SURFONIC L24-3™ surfactant were charged to the reaction vessel and heated to above 100° C.

with stirring to form a homogeneous mixture. Subsequently, the reaction vessel was charged with 40% water, heated to above 100° C. with stirring to form a homogeneous mixture, followed by cooling to room temperature with stirring, resulting in a white cream, with a soft paste texture, indicative of a water-in-oil emulsion.

Example 29

This example shows that an aqueous-based emulsion made from ETPA in the absence of a surfactant may be difficult to make if the water is added initially to the formulation. A reaction vessel, equipped with a magnetic stir bar, was charged with (by percentage of final weight mixture) 30.51% DRAKEOL 7™ mineral oil, 10.17% PC0063-4 (contains 40% SYLVAGEL 6000™ ester-terminated polyamide resin, 20% PARAFLINT H4™ microcrystalline wax, 20% MAGIESOL M-47™ white mineral oil and 20% ester, and 49.15% water, heated to above 100° C. with stirring to form a homogeneous mixture, followed by cooling to room temperature with stirring, resulting in two separate layers. A white cream, with a soft paste texture, was observed on top while a clear liquid remained in the bottom layer.

Example 30

Samples of the suspension produced in Examples 16 and 17, as well as samples of PC0063-3 (see Example 22) and PC0063-4 (see Example 18) were applied to cold rolled steel coupons with a finger and allowed to sit on the coupons overnight. Samples PC0063-3 and PC0063-4 were hard, white pastes while the suspensions of Examples 16 and 17 were soft, white pastes. The soft pastes gave a greasy texture when applied to the coupon while the hard pastes were less greasy to the touch. All four formulations were removed from the coupons using a cloth and gave a shiny appearance on the steel coupons, when compared with the control (untreated coupon).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A composition comprising polymerized fatty acid-based polyamide, organic solvent, and water, wherein the polyamide is a gellant for the organic solvent.

2. The composition of claim 1 having an aqueous continuous phase and an organic discontinuous phase.

3. The composition of claim 1 having an organic continuous phase and an aqueous discontinuous phase.

4. A composition of claim 1 comprising:

(a) a discontinuous aqueous phase;
(b) a continuous organic phase comprising an organic solvent that is a liquid at room temperature, and is either insoluble in water or is soluble in water to an extent of less than about 1.0 gram organic solvent per 100 grams water at 25° C.; and
(c) polyamide gellant selected from ester-terminated polyamide or amide-terminated polyamide.

5. The composition of claim 1 wherein the polyamide is an ester-terminated polyamide of formula (1):

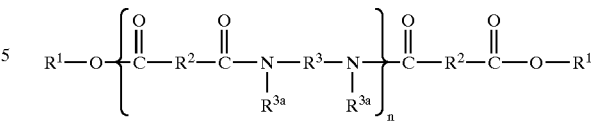

wherein n designates a number of repeating units such that ester groups are from 10% to 50% of the total of the ester and amide groups; $R^1$ at each occurrence is independently selected from an alkyl or alkenyl group containing at least 4 carbon atoms; $R^2$ at each occurrence is independently selected from a $C_{4-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C^{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

6. The composition of claim 1 wherein the polyamide is a tertiary amide-terminated polyamide of formula (2):

$$\begin{matrix} R^4 \\ \diagdown \\ N \\ \diagup \\ R^4 \end{matrix} \left[ \begin{matrix} O & & O \\ \| & & \| \\ C-R^5-CN-R^6-N \\ & & | & & | \\ & & R^{6a} & & R^{6a} \end{matrix} \right]_n \begin{matrix} O & & O & R^4 \\ \| & & \| & \diagup \\ C-R^5-C-N \\ & & & \diagdown \\ & & & R^4 \end{matrix} \quad (2)$$

wherein n designates a number of repeating units such that terminal amide groups constitute from 10% to 50% of the total amide groups; $R^4$ at each occurrence is independently selected from a $C_{1-22}$ hydrocarbon group; $R^5$ at each occurrence is independently selected from a $C_{2-42}$ hydrocarbon group; $R^6$ at each occurrence is independently selected from an organic group containing at least two carbon atoms in addition to hydrogen atoms, and optionally containing one or more oxygen and nitrogen atoms; and $R^{6a}$ at each occurrence is independently selected from hydrogen, $C_{1-10}$ alkyl and a direct bond to $R^6$ or another $R^{6a}$ such that the N atom to which $R^6$ and $R^{6a}$ are both bonded is part of a heterocyclic structure defined in part by $R^{6a}$—N—$R^6$.

7. The composition of claim 1 wherein the organic solvent is immiscible with water.

8. The composition of eleims claim 1 wherein the organic solvent has at least eight carbons.

9. The composition of claim 1 wherein the organic solvent comprises a hydrocarbon.

10. The composition of claim 1 wherein the polyamide is 1–30% of the total weight of the composition.

11. The composition of claim 1 wherein the organic solvent is 10–70% of the total weight of the composition.

12. The composition of claim 1 wherein the water is 20–90% of the total weight of the composition.

13. The composition of claim 1 in the form of a self-supporting cream that does not contain a surfactant.

14. The composition of claim 1 further comprising a surfactant.

15. The composition of claim 1 further comprising wax.

16. The composition of claim 1 formulated as a cosmetic product or a personal care product.

17. The composition of claim 1 formulated as a polish for a solid surface.

18. A method for preparing a water-in-oil emulsion comprising heating components comprising the polymerized fatty acid-based polyamide, organic solvent, and water of claim 1 to a provide a fluid mixture; stirring the fluid mixture to provide a macroscopically homogenous mixture; and cooling the homogeneous mixture to room temperature to provide an emulsion.

19. A method for preparing a water-in-oil emulsion according to claim 18, comprising the ordered steps of:
(a) forming an initial mixture wherein the organic solvent is combined with the polyamide with stirring;
(b) heating the initial mixture to provide a single fluid phase in which the organic solvent and polyamide are distributed evenly throughout the phase; and
(c) adding water with stirring to the single fluid phase (b) to provide an emulsion.

20. A method for preparing a water-in-oil emulsion according to claim 18, comprising the ordered steps of:
(a) combining the organic solvent, water, and polyamide, with stirring, to provide an initial mixture;
(b) heating the initial mixture to about 90–120° C. to form a fluid phase in which components are distributed evenly throughout the phase;
(c) allowing the mixture formed in (b) to cool to room temperature.

* * * * *